United States Patent [19]
Okada et al.

[11] Patent Number: 5,595,986
[45] Date of Patent: Jan. 21, 1997

[54] STABLY STORABLE AND READILY WATER SOLUBLE COMPOSITION OF CEPHALOSPORIN FOR INJECTIONS

[75] Inventors: Makoto Okada; Masaki Takahashi; Kaoru Hosoi; Shokichi Nakajima, all of Yokohama, Japan

[73] Assignee: Meiji Seika Kaisha, Ltd., Tokyo, Japan

[21] Appl. No.: 510,342

[22] Filed: Aug. 2, 1995

[30] Foreign Application Priority Data

Aug. 3, 1994 [JP] Japan .................................. 6-182378

[51] Int. Cl.⁶ .................................. A61K 31/545
[52] U.S. Cl. .......................... 514/202; 514/206
[58] Field of Search ..................... 514/202, 206

[56] References Cited

U.S. PATENT DOCUMENTS 4,839,350  6/1989  Atsumi et al. ..................... 514/202

OTHER PUBLICATIONS

Chemical Abstracts AN 87:90680 (Gottstein et al, 1977).

Primary Examiner—Marianne M. Cintins
Assistant Examiner—Keith MacMillan
Attorney, Agent, or Firm—Larson & Taylor

[57] ABSTRACT

A stably storable and readily water soluble composition for use in preparing injections and containing Cefditoren, namely a cephalosporin of the formula

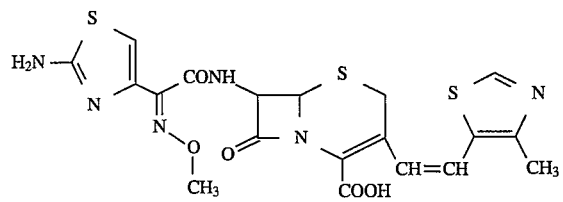

is now provided, which composition comprises a physical mixture of Cefditoren or a non-toxic salt thereof with a proportion of arginine and/or lysine and/or a non-toxic salt thereof. This new composition of Cefditoren can be stored for long periods of time without discoloration and without undesirable reduction in the antibacterial activity, and the composition can be dissolved completely and quickly in water.

6 Claims, No Drawings

STABLY STORABLE AND READILY WATER SOLUBLE COMPOSITION OF CEPHALOSPORIN FOR INJECTIONS

FIELD OF THE INVENTION

This invention relates to a new, stably storable and readily water soluble composition comprising as active ingredient a cephalosporin known as Cefditoren, which may be used to prepare injections, namely injectable aqueous solutions by dissolving it in water, and which is effectively utilizable in the field of pharmaceutics. This invention also embraces a powdery mixture of said cephalosporin, i.e., Cefditoren with arginine and/or lysine in the form of a lyophilized preparation.

BACKGROUND OF THE INVENTION

A cephalosporin represented by the following formula

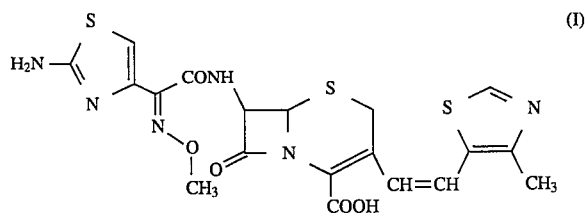

namely, (6R,7R)-7-[(Z)-2-(2-aminothiazol-4-yl) -2-methoxy-imino acetamido]-3-[(Z)-2-(4-methylthiazol-5-yl)ethenyl]-8-oxo-5-thia-1-azabicyclo[4.2.0]oct-2-ene-2-carboxylic acid is known as "Cefditoren", a generic name, and also is nominated as 7-[methoxyimino-2- (2-aminothiazol-4-yl) acetamido]-3-[2- (4-methylthiazol-5-yl) vinyl]-3 -cephem-4-carboxylic acid in U.S. Pat. No. 4,839,350, Japanese patent No. 1698887 (Japanese patent publication "Kokoku" No. Hei-3-64503 published 7 October 1991) and European patent No. 0175610. The cephalosporin having the above formula (I) or a pharmaceutically acceptable salt thereof has a broad range of antibacterial spectra against gram-positive bacteria and gram-negative bacteria and can exhibit a high antibacterial activity against *Staphylococcus aureus, Klebsiella pneumoniae* and *Haemophilus influenzae* in particular, and thus is promising for use as injections.

While, it is known that arginine salt or lysine salt of certain acidic cephalosporins may be formulated into intramuscularly or subcutaneously injectable preparation with no substantial pain (U.S. Pat. No. 3,984,403), that a stable injection containing a certain cephalosporin together with lactose, citric acid, arginine and sodium chloride may be prepared (U.S. Pat. No. 5,254,545), and that several, crystalline and temperature-stable acid addition salts of 7-[α-(2-aminothiazol-4-yl)-α-(Z)-methoxyiminoacetamido]-3-[(1-methyl-1-pyrrolidino)methyl]-3-cephem-4-carboxylate may be formulated into the form of a physical admixture with lysine and/or arginine acting as a buffering agent and this admixture may be diluted with water to give an injectable preparation (U.S. Pat. Nos. 4,910,301; 4,994,451 and 5,244, 891, and Japanese patent application first publication "Kokai" No. Hei-2-9885 laid open on Jan. 12, 1990). Cefditoren is not so highly stable to a fully satisfactory extent upon its storage when it is stored at ambient temperatures under dry air for long periods of time. Thus, Cefditoren can exhibit such low storage-stabilities that it can be discolored to a yellow color from its initial, faintly yellow to color less appearance and can be decomposed to an extent to show an undesirable reduction in its antibacterial activity, when Cefditoren has been stored at ambient temperatures under dry air or nitrogen gas for a long period of time. Cefditoren itself is of a low solubility in water at ambient temperatures, and a large amount of Cefditoren cannot be dissolved completely in water so that a clear aqueous solution containing Cefditoren at its medicinally effective concentration is difficult to be prepared.

In an attempt to prepare an injectable preparation containing Cefditoren or its pharmaceutically acceptable salt which may be dissolved in water just upon use to make up an injectable aqueous solution containing the cephalosporin, we, the present inventors, have made many experiments wherein Cefditoren or a pharmaceutically acceptable salt thereof alone is dissolved in water without addition of any stabilizing agent for the cephalosporin and the resulting aqueous solution is adjusted to a pH of 6.0–7.5 by addition of 0.1N aqueous sodium hydroxide or 0.1N aqueous hydrochloric acid and then lyophilized to afford a powdery preparation which is to be dissolved in a volume of injection-grade water upon use as an injectable aqueous solution, and which may be termed as "injectable powdery preparation for dissolution upon use", and wherein the powdery preparation as afforded is stored at ambient temperatures under dry air for long periods of time. It has been observed that the above-mentioned powdery preparation after the storage has been discolored to a yellow color and also been decomposed to show a reduction in its antibacterial potency as compared to its initial antibacterial potency of the powdery preparation before the storage, and that small quantities of water-insoluble matters can be left undissolved when the powdery preparation prepared as above is tried to be dissolved in water at room temperature before and after the storage. Thus, we have now found that the storage-stability of Cefditoren or a pharmaceutically acceptable salt thereof to be mixed in commercially distributable injections of Cefditoren is needed to be enhanced much as possible by devising a new measure to modify the composition or formulation of an injectable powdery preparation containing Cefditoren, in order to ensure that Cefditoren or a pharmaceutically acceptable salt thereof can be utilized safely and satisfactorily in a form of an injectable powdery preparation which is available in hospitals.

Therefore, an object of this invention is to provide such a new, stably storable and readily water soluble composition containing Cefditoren or a salt thereof, which is supplied in the form of a powdery preparation to be formulated into an injectable aqueous solution by dissolving in water by experts of the medicinal field in hospitals. Another object of this invention is to provide a new method for enhancing the storage-stability+of Cefditoren or a salt thereof present in a powdery composition containing the cephalosporin.

DETAILED DESCRIPTION OF THE INVENTION

The present inventors have made extensive investigations with a view towards providing a new, stably storable and readily water soluble powdery composition comprising Cefditoren or a pharmaceutically acceptable salt thereof as active ingredient, which is supplied in the form of so-called "injectable powdery preparation for dissolution upon use" and may be readily dissolved in injection-grade water by experts of hospitals to make up an injectable aqueous solution of Cefditoren or its salt. As a result, the present inventors have now found that when Cefditoren or a pharmaceutically acceptable salt thereof is physically and intimately mixed with at least one of arginine, lysine or a pharmaceutically acceptable acid addition salt thereof in an amount or a proportion such that 1 part by weight of Cefditoren or a salt thereof is mixed with 0.1 parts or more by weight of arginine or with 0.2 parts or more by weight of lysine, the resulting physical mixture of Cefditoren or its salt with arginine and/or lysine (or their pharmaceutically acceptable acid additions salts)is able to exhibit enhanced storage-stabilities such that said physical mixture does bring about no or substantially no discoloration and is not decomposed to a substantial extent, and also have found that said physical mixture can be dissolved completely and quickly in water at ambient temperatures before and after a storage thereof. On the basis of these findings, the present invention has now been completed.

According to a first aspect of this invention, therefore, there is provided a stably storable and readily water soluble composition for use in preparing injections and comprising as active ingredient a cephalosporin represented by the following formula

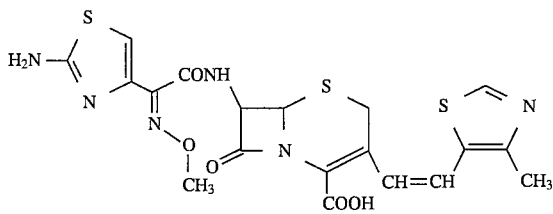

namely, (6R,7R)-7-[(Z)-2-(2-aminothiazol-4-yl)-2-methoxyiminoacetamido]-3-[(Z)-2-(4-methylthiazol-5-yl)ethenyl]-8-oxo-5-thia-1-azabicyclo[4.2.01]oct-2-ene-2-carboxylic acid or a pharmaceutically acceptable salt thereof, and capable of being stored at ambient temperatures for long periods without bringing about a substantial discoloration and without involving a substantial decomposition of the cephalosporin of the formula (I), which composition comprises a physical mixture of the cephalosporin of the formula (I) or a pharmaceutically acceptable salt thereof with at least one of arginine, lysine or a pharmaceutically acceptable salt thereof, and in which the amount of arginine, lysine or a pharmaceutically acceptable salt thereof present in said mixture is effective to prevent the compound of the formula (I) or a salt thereof from being discolored and decomposed to a substantial extent during a long-time storage of the composition at ambient temperatures and also allow the whole composition to be completely dissolved in water at ambient temperatures before and after a storage of the composition at ambient temperatures.

In the stably storable and readily water soluble composition containing Cefditoren or a salt thereof according to the first aspect of this invention, the arginine and/or lysine and/or the pharmaceutically acceptable acid addition salt thereof as incorporated in the specified proportions in said composition is considered to be unexpectably able to act not only a stabilizer for Cefditoren against its decomposition during the storage, but also as an inhibitor for preventing Cefditoren from being discolored to an undesirable extent during the storage of Cefditoren. Besides, the arginine component and/or lysine component presented in the composition of this invention is able to assist or allow the Cefditoren component to be dissolved quickly and completely in water before and after a storage of the composition.

A pharmaceutically acceptable salt of Cefditoren usable and incorporatable in the composition of this invention may include a salt (carboxylate) of Cefditoren with a pharmaceutically acceptable alkali metal such as sodium or potassium; a pharmaceutically acceptable alkaline earth metal such as calcium or magnesium, or ammonium anion, and a base-addition salt of Cefditoren with a pharmaceutically acceptable organic base such as trimethylamine, triethylamine, pyridine or dicyclohexylamine, as well as an acid-addition salt of Cefditoren with a pharmaceutically acceptable organic acid such as formic acid, acetic acid, maleic acid, tartaric acid, p-toluenesulfonic acid or the like, or a pharmaceutically acceptable inorganic acid such as hydrochloric acid, sulfuric acid or phosphoric acid; and also an acid-addition salt with an amino acid such as arginine, asparatic acid or glutamic acid.

Arginine and lysine usable and incorporatable in the composition of this invention may each be either in the form of D-isomer, or in the form of L-isomer or in the form of DL-compound (namely, the racemic mixture). Arginine and lysine may be used as a pharmaceutically acceptable (non-toxic) salt thereof, including an acid-addition salt thereof with a pharmaceutically acceptable inorganic acid such as hydrochloric acid, sulfuric acid or phosphoric acid.

The amount or proportion of arginine or lysine as incorporated in the composition of this invention is necessary to be such those that 0.1 parts or greater of arginine or 0.2 parts or greater of lysine is presented per 1 part of Cefditoren or a pharmaceutically acceptable salt thereof on the weight basis. However, no strict limitation is imposed on the upper limit of the amount or proportion of arginine or lysine incorporated in the composition of this invention.

When the amount of arginine is less than 0.1 parts by weight per 1 part by weight of Cefditoren or a salt thereof, or when the amount of lysine is less than 0.2 parts by weight per 1 part by weight of Cefditoren or a salt thereof present in the composition of this invention, there cannot be achieved the intended effects of arginine or lysine that the arginine or lysine component effectively acts to make the composition of this invention storable stably to a sufficient extent during the storage of the composition and also render the whole composition completely and readily soluble in water before and after a storage of the composition. Thus, such composition containing an insufficient amount or proportion of arginine or lysine relative to the proportion of Cefditoren or a salt thereof present therein can has been discolored yellowish objectionably at the end of the storage with involving a decomposition of the Cefditoren component and also cannot be dissolved completely and quickly in water, so that the such composition as yellow-discolored after a storage will exhibit an undesirable reduction in the antibacterial activity as compared to the initial value of the antibacterial activity of the composition before the storage and also cannot be dissolved completely in water but will leave some solid matters which remain undissolved in water even under vigorous stirring.

With the composition of this invention, therefore, it is suitable that the amount or proportion of arginine or lysine as incorporated in the composition is chosen within a desirable range in view of the solubility of arginine, lysine or a salt thereof in water. Normally, the amount or proportion of arginine or lysine as incorporated in the composition of this invention may be so chosen that the weight ratio of Cefditoren or a salt thereof to arginine is in a range of 1.0:0.1 to 1.0:2.0, preferably in a range of 1.0:0.1 to 1.0:1.0 or that the weight ratio of Cefditoren or a salt thereof to lysine is in a range of 1.0:0.2 to 1.0:2.0, preferably in a range of 1.0:0.2 to 1.0:1.0.

In the composition containing Cefditoren or a salt thereof according to this invention, the proportion of Cefditoren, namely the cephalosporin of the formula (I) or a pharmaceutically acceptable salt thereof present in the composition may be in a range of up to 90%, preferably in a range of 25% to 90%, especially 40% to 90%, by weight, based on the weight of the whole composition.

Furthermore, the composition of this invention, if desired, may further contain varying amounts of one or more of additives or supplemental components, for example, a pH-adjustor such as sodium hydroxide or hydrochloric acid; an extender such as glucose or dextran; buffering agent such as potassium di-hydrogen phosphate; an isotonic agent such as sodium chloride and so on, which may ordinarily be used and incorporated in conventional preparations for injections.

As a process for producing the composition of this invention, it is possible to carry out such a process wherein Cefditoren or a non-toxic salt thereof as well as at least one of arginine, lysine and a pharmaceutically acceptable salt thereof are dissolved in a volume of water, optionally along with one or more of desirable additive or supplemental components, followed by lyophilizing or drying the resulting aqueous solution under reduced pressure to afford a dry and powdery physical mixture of the Cefditoren component with the arginine and/or lysine components which optionally may further contain the additive components. Alternatively, it is possible to mix finely divided particles of Cefditoren with finely divided particles of arginine and/or lysine uniformly so as to give an intimately and uniformly mixed and powdery physical mixture of the Cefditoren component with the arginine and/or lysine components.

It is preferred that the composition of this invention as produced by the process set out in the above takes the form of a lyophilized powdery preparation. The production of the composition of this invention which is in the form of such a lyophilized powdery preparation may be conducted by a generally known method for the lyophilization. For instance, the composition of this invention in the form of the lyophilized powder may conveniently be obtained by a method which comprises dissolving the required amounts of Cefditoren or a non-toxic salt thereof as well as arginine and/or lysine into a volume of injection-grade water, adjusting the resulting aqueous solution to an appropriate pH value, e.g., in a range of pH of 6.0 to 7.5 by addition of a pharmaceutically acceptable acid such as hydrochloric acid or a pharmaceutically acceptable alkali metal hydroxide, then filtering the solution under sterile conditions, placing aliquots of the sterile solution (the filtrate) separately into vials, lyophilizing the solution in the vials by a conventional method of lyophilization, and then sealing the vials hermetically with caps.

In the composition according to the first aspect of this invention as described hereinbefore, the abovementioned noticeable instabilities upon storage of Cefditoren or a non-toxic salt thereof can have been reduced or eliminated by admixing Cefditoren intimately with the specified proportion of arginine and/or lysine. According to a second aspect of this invention, therefore, there is provided a method for reducing or eliminating the storage-instabilities of a cephalosporin represented by the formula (I) defined hereinbefore, or a pharmaceutically acceptable salt thereof such that the cephalosporin of the formula (I) or the salt thereof can be decomposed during a long-time storage at ambient temperatures with bringing about a substantial discoloration, which method comprises providing a dry, physical mixture of the cephalosporin of the formula (I) or the salt thereof with at least one of arginine, lysine or a pharmaceutically acceptable salt thereof in such a proportion that the weight ratio of the cephalosporin of the formula (I) or the salt thereof to arginine is in a range of 1.0:0.1 to 1.0:2.0 or the weight ratio of the cephalosporin of the formula (I) or the salt thereof to lysine is in a range of 1.0:0.2 to 1.0:2.0, and then storing the resulting physical mixture at ambient temperatures under dry conditions for a long period of time for storage.

The pharmaceutically acceptable salt of Cefditoren, that is, the cephalosporin of the formula (I) as well as the pharmaceutically acceptable salt of arginine or lysine usable in the method of the second aspect of this invention are same as those which are respectively referred to in respect of the first aspect of this invention. The dry physical mixture of Cefditoren or a salt thereof with arginine and/or lysine to be provided in the method of the second aspect of this invention may preferably be in the form of a lyophilized powdery preparation which can be produced in the same manner as described hereinbefore in respect of the composition according to the first aspect of this invention.

The following Examples are now given below in order to demonstrate that several samples of lyophilized powdery preparations which are constituted by the composition of this invention comprising Cefditoren or a non-toxic salt thereof as active ingredient and varying amounts of L-arginine or L-lysine (the hydrochloride) chloride) are effectively able to exhibit an enhanced stability upon storage as well as an enhanced solubility of the whole preparation in water before or after a storage even at an elevated temperature, and that these meritable effects of attaining the enhanced storage-stability and the enhanced water-solubility for the tested preparations are obtained by the incorporation of the specified proportions of arginine or lysine in the preparations. However, this invention is not limited in any way to the following Examples.

EXAMPLE 1

An aqueous solution containing 2.5 g of Cefditoren dissolved in 30 ml of injection-grade water was prepared and then added with 0.25 g, 0.5 g or 1 g of L-arginine or with 0.625 g, 1.25 g or 2.0 g of L-lysine (as the hydrochloride). The resulting aqueous solution of Cefditoren and L-arginine or L-lysine was then adjusted to pH 7.4 by addition of 0.1N aqueous solution of sodium hydroxide or 0.1N aqueous solution of hydrochloric acid and then diluted with injection-grade water to 50 g. The aqueous solution so prepared was filtered under sterile conditions, and the filtrate was filled in 5 g-aliquots in 10-ml vials and lyophilized. The vials containing the lyophilized powdery preparations so produced were sealed hermetically with caps. The lyophilized powdery preparations in the capped vials were stored as the test samples according to this invention.

Further, an aqueous solution containing 2.5 g of Cefditoren dissolved in 30 ml of injection-grade water was prepared and adjusted to pH 7.4 by addition of 0.1N aqueous solution of sodium hydroxide or 0.1 N aqueous solution of hydrochloric acid. The resulting pH-adjusted aqueous solution was diluted with injection-grade water to 50 g. The solution was likewise filtered under sterile conditions, and the filtrate was filled in 5 g-aliquots in 10-ml vials and lyophilized. The vials containing the lyophilized powdery preparations so produced were sealed hermetically with caps. The lyophilized powdery preparations in the capped vials were stored as comparative test samples not according to this invention.

The test samples according to this invention, as well as the comparative test samples were stored at 60° C. for one month while these samples were kept in the capped vials. After the storage, changes occurring in the appearance of the test samples after the storage were observed, and the water-solubility and stability of the test samples were estimated.

In order to estimate the solubility of the test samples in water, each oft he test samples beforeand after the storage was mixed with injection-grade water (3 ml) and soon the resulting mixture was weakly agitated for 20 or 70 seconds, immediately followed by observing whether the lyophilized powder of the test sample could be quickly and completely dissolved in the water in 20 seconds or a little longer without leaving any solid matters undissolved in water.

In order to estimate the stability of the test samples, percentages (%) of the residual quantity of Cefditoren in the test samples after the storage were determined by a high performance liquid chromatography, and the changes in the appearance of the test samples were observed in terms of the degree of discoloration as produced in the samples after the storage. The percentages of the residual quantity of Cefditoren in the test samples was determined by subjecting the test samples to a high performance liquid chromatography (HPLC) with octadecylsilylized Silica Gel (a product saled from YMC Co. Ltd., Japan) as the immobile phase and with a mixed solvent of 0.1% aqueous ammonium acetate-methanol (65:35) as the mobile phase, and measuring the optical density of the eluate at 230 nm and calculating the ratio of the area under the absorption peak curve as measured for the test sample to the area under the absorption peak curve as measured for internal standard substance, as assumed that the residual quantity (%) of Cefditoren in the test samples amounted to 100% directly before the storage. The test results obtained are summarised in Table 1 below.

TABLE 1

| Arginine or lysine as mixed with Cefditoren | Weight ratio between Cefditoren and arginine or lysine | Changes* in appearance (Degree of discoloration) | Solubility** before and after the storage | Residual quantity (%) of Cefditoren |
|---|---|---|---|---|
| None (comparative) | 0 | (+) | (+) | 87.4 |
| L-arginine (this invention) | 1:0.1 | (−) to (±) | (−) | 90.4 |
| | 1:0.2 | (−) to (±) | (−) | 93.0 |
| | 1:0.4 | (−) | (−) | 95.4 |
| L-lysine (as hydrochloride) (this invention) | 1:0.25 | (±) | (−) | 91.4 |
| | 1:0.5 | (−) to (±) | (−) | 93.3 |
| | 1:0.8 | (−) | (−) | 95.5 |

Notes:
* Changes in appearance are evaluated in the following scales:-
(+) denotes that the test sample after storage had been discolored to a noticeably yellow color.
(±) denotes that the test sample after storage had been discolored nearly to a thinnly yellow color.
(−) denotes that the test sample after storage had received no discoloration but kept the initial, faintly yellow to colorless appearance.
** Solubility are evaluated in the following scales:-
(+) denotes that the test sample before and after storage could not be dissolved completely in water but left solid matters or precipitate undissolved in water.
(−) denotes that the test sample before and after storage could be dissolved completely and quickly in water in about 20 seconds without leaving any solid matters.

From the results of Table 1 above, it is evident that the admixing of arginine or lysine with Cefditoren is able to prevent Cefditoren from bringing about changes in the appearance of the preparation, particularly from being discolored objectionably during the storage even at elevated temperatures, and that the admixing of arginine or lysine with Cefditoren is also able to inhibit Cefditoren from being decomposed during the storage and further is able to enhance the solubility of Cefditoren in water.

EXAMPLE 2

An aqueous solution of 2.5 g of Cefditoren dissolved in 30 ml of injection-grade distilled water was prepared and then added with 1 g of L-arginine under stirring. The resulting aqueous solution was subsequently adjusted to pH 7.4 by addition of 0.1 N aqueous solution of sodium hydroxide or 0.1 N aqueous solution of hydrochloric acid and then diluted with injection-grade distilled water to 50 g. The aqueous solution so prepared was filtered under sterile conditions, and the filtrate was filled in 5 g-aliquots in 10 ml-vials and lyophilized. The vials containing the lyophilized powdery preparation so produced were sealed hermetically with caps. In this way, a lyophilized powdery preparation for injection containing Cefditoren was obtained, which was ready for use as injections after dissolving it in injection-grade water in hospitals.

EXAMPLE 3

An aqueous solution of 2.5 g of Cefditoren dissolved in 30 ml of injection-grade water was prepared and then added with 1.6 g of L-lysine under stirring. The resulting aqueous solution was adjusted to pH 7.4 by addition of 0.1N aqueous solution of sodium hydroxide or 0.1N aqueous solution of hydrochloric acid and then diluted with injection-grade water to 50 g. The aqueous solution so prepared was filtered under sterile conditions, and the filtrate was filled in 5 g-aliquots in 10 ml-vials and lyophilized. The vials containing the lyophilized powdery preparation so produced were sealed hermetically with caps.

We claim:

1. A stably storable and readily water soluble composition for use in preparing injections and comprising as active ingredient sodium or potassium salt of a cephalosporin having the formula

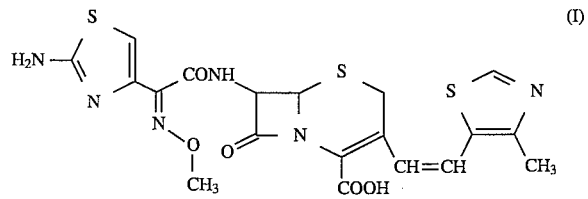

and the name, (6R,7R)-7-[(Z)-2-(2-aminothiazol-4-yl)-2-methoxyiminoacetamido]-3-[(Z)-2-(4-methylthiazol-5-yl)ethenyl]-8-oxo-5-thia-1-azabicyclo[4.2.0]oct-2-ene-2-carboxylic acid, and capable of being stored at ambient temperatures without bringing about a substantial discoloration and without involving a substantial decomposition of the cephalosporin of the formula (I), which composition comprises a dry physical mixture of the sodium or potassium salt of the cephalosporin of formula (I) with at least one of arginine, lysine or a pharmaceutically acceptable salt thereof, and in which the weight ratio of said cephalosporin of formula (I) to arginine is in a ratio of 1.0:0.1 to 1.0:2.0 or the weight ratio of said cephalosporin of formula (I) to lysine is in a range of 1.0:0.2 to 1.0:2.0 and in which the amount of arginine, lysine or a pharmaceutically acceptable salt thereof present in the mixture is effective to prevent the salt of the compound of the formula (I) from being discolored and decomposed to a substantial extent during a storage of the composition at ambient temperatures and also allow the composition to be completely dissolved in water at ambient temperatures before and even after the storage of the composition at ambient temperatures.

2. A composition as claimed in claim 1, in which the weight ratio of the cephalosporin of the formula (I) to arginine present in said mixture is in a range of 1.0:0.1 to 1.0:1.0.

3. A composition as claimed in claim 1, in which the weight ratio of the cephalosporin of the formula (I) to lysine present in said mixture is in a range of 1.0:0.2 to 1.0:1.0.

4. A composition as claimed in claim 1, which is in the form of a lyophilized powdery preparation.

5. A composition as claimed in claim 1, in which said mixture optionally contains further at least one of pH-adjuster, extender, buffering agent and isotonic agent conventionally usable in injectable preparations.

6. A method for making readily soluble in water sodium or potassium salt of the cephalosporin having formula (I) defined in claim 1 and also for reducing or eliminating such storage-instabilities of the sodium or potassium salt of said cephalosporin that the salt of the cephalosporin can not be decomposed with substantial discoloration during a storage at ambient temperatures, which method comprises providing a dry, physical mixture of the sodium or potassium salt of the cephalosporin with at least one of arginine, lysine or a pharmaceutically acceptable salt thereof by mixing the sodium or potassium salt of said cephalosporin with arginine, lysine and/or a pharmaceutically acceptable salt thereof, in such a proportion that the weight ratio of said cephalosporin of formula (I) to arginine is in a range of 1.0:0.1 to 1.0:2.0 or the weight ratio of said cephalosporin of formula (I) to lysine is in a range of 1.0:0.2 to 1.0:2.0, and then storing the resulting physical mixture at ambient temperatures under dry conditions.

* * * * *